United States Patent
Lin et al.

(10) Patent No.: US 6,562,014 B2
(45) Date of Patent: May 13, 2003

(54) DEVICE AND METHOD FOR ENHANCING TRANSDERMAL FLUX OF AGENTS BEING SAMPLED

(75) Inventors: Wei-Qi Lin, Palo Alto, CA (US); Michel J. N. Cormier, Mountain View, CA (US); Felix Theeuwes, Los Altos Hills, CA (US)

(73) Assignee: Alza Corporation, Palo Alto, CA (US)

( * ) Notice: Subject to any disclaimer, the term of this patent is extended or adjusted under 35 U.S.C. 154(b) by 0 days.

(21) Appl. No.: 09/737,882

(22) Filed: Dec. 14, 2000

(65) Prior Publication Data

US 2002/0077584 A1 Jun. 20, 2002

Related U.S. Application Data (60) Provisional application No. 60/172,357, filed on Dec. 16, 1999.

(51) Int. Cl.[7] .................................................. A61M 1/00
(52) U.S. Cl. ..................... 604/317; 604/319; 604/329; 600/562; 600/578; 600/584
(58) Field of Search ............................ 604/311, 318, 604/319, 320–329; 600/562, 573, 577, 578, 579, 583, 584

(56) References Cited

U.S. PATENT DOCUMENTS

| | | | |
|---|---|---|---|
| 3,814,097 A | 6/1974 | Ganderton et al. | 128/268 |
| 3,964,482 A | 6/1976 | Gerstel et al. | 128/260 |
| 4,287,819 A * | 9/1981 | Emerit | 99/472 |
| 4,627,445 A | 12/1986 | Garcia et al. | 128/770 |
| 5,054,499 A | 10/1991 | Swierczek | 128/770 |
| 5,070,886 A | 12/1991 | Mitchen et al. | 128/771 |
| 5,161,532 A | 11/1992 | Joseph | 128/635 |
| 5,201,324 A | 4/1993 | Swierczek | 128/770 |
| 5,231,993 A * | 8/1993 | Haber et al. | 128/770 |
| 5,250,023 A | 10/1993 | Lee et al. | 604/20 |
| 5,279,544 A | 1/1994 | Gross et al. | 604/20 |
| 5,320,607 A | 6/1994 | Ishibashi | 604/115 |
| 5,368,047 A * | 11/1994 | Suzuki et al. | 128/765 |
| 5,402,798 A | 4/1995 | Swierczek et al. | 128/770 |
| 5,417,206 A | 5/1995 | Kaneyoshi | 128/632 |
| 5,441,490 A | 8/1995 | Svedman | 604/289 |
| 5,505,212 A | 4/1996 | Keljmann et al. | 128/771 |
| 5,582,184 A | 12/1996 | Erickson et al. | 128/763 |
| 5,682,233 A | 10/1997 | Brinda | 356/246 |
| 5,746,217 A | 5/1998 | Erickson et al. | 128/760 |
| 5,762,640 A * | 6/1998 | Kajiwara et al. | 604/313 |
| 5,820,570 A | 10/1998 | Erickson et al. | 600/573 |
| 5,882,317 A * | 3/1999 | Saito et al. | 600/578 |
| 6,050,988 A * | 4/2000 | Zuck | 604/890.1 |
| 6,132,449 A * | 10/2000 | Lum et al. | 606/181 |
| 6,155,992 A | 12/2000 | Hernning et al. | 600/583 |
| 6,219,574 B1 * | 4/2001 | Cormier et al. | 600/578 |
| 6,230,051 B1 * | 5/2001 | Cormier et al. | 604/20 |

FOREIGN PATENT DOCUMENTS

| | | | |
|---|---|---|---|
| WO | WO 96/37155 | 11/1996 | A61B/17/20 |
| WO | WO 96/37256 | 11/1996 | A61N/1/30 |
| WO | WO 97/14452 | 4/1997 | A61M/1/08 |
| WO | WO 97/48440 | 12/1997 | A61N/1/30 |
| WO | WO 99/27852 | 6/1999 | A61B/5/103 |

\* cited by examiner

*Primary Examiner*—Charles G. Freay
*Assistant Examiner*—John F. Belena
(74) *Attorney, Agent, or Firm*—Owen J. Bates

(57) ABSTRACT

A transdermal agent sampling device is provided. The sampling device is comprised of a microblade array and a device for applying a partial vacuum. The microblade array comprises a sheet having a plurality of microblades for piercing the skin to a very shallow depth (i.e., 25 μm to 400 μm) to create microslits in the outermost stratum corneum layer of the skin. The partial vacuum applying device applies a partial vacuum in the range of about 0.1 to about 0.8 atm, and preferably about 0.3 to about 0.7 atm, for sampling a body analyte such as glucose in interstitial fluid. The partial vacuum is applied for a period of about 2 to about 30 seconds, and preferably about 5 to about 15 seconds. The interstial fluid is analyzed for body analyte (e.g., glucose) content or concentration.

25 Claims, 7 Drawing Sheets

DEVICE AND METHOD FOR ENHANCING TRANSDERMAL FLUX OF AGENTS BEING SAMPLED

This application claims the benefit of Provisional application Ser. No. 60/172,357, filed Dec. 16, 1999.

FIELD OF THE INVENTION

The present invention relates to transdermal agent sampling. More particularly, this invention relates to the transdermal sampling of agents, such as glucose, body electrolytes and substances of abuse, such as but not limited to alcohol and illicit drugs. The present invention uses skin-piercing microblades to enhance the transdermal flux of the agents during transdermal sampling and negative pressure (i.e., partial vacuum) devices which assist the transdermal efflux of fluid (i.e., interstitial fluid) carrying the agent/analyte to be sampled.

BACKGROUND OF THE INVENTION

Obtaining a droplet of blood for the purpose of sampling a constituent (e.g., glucose) is commonly achieved by piercing the skin using a lancet or other blade-like element. Many such skin piercing devices are spring-driven so that the piercing is accomplished automatically by a pen or similar spring-loaded device. See for example, Suzuki et al. U.S. Pat. No. 5,368,047.

May blood sampling devices also apply suction to the wound following piercing by the lancet. The suction assists in obtaining a blood sample of appropriate size for testing blood components such as glucose. See for example, Suzuki et al. U.S. Pat. No. 5,368,047; Swierczek U.S. Pat. No. 5,054,499; Ishibashi U.S. Pat. No. 5,320,607; Haber et al., U.S. Pat. No. 5,231,993; and Swierczek U.S. Pat. No. 5,201,324.

A partial vacuum applied to the skin has also been used in order to create suction blisters wherein the upper epidermis layer of the skin is separated from the dermis layer of the skin. To separate the epidermis from the dermis, a partial vacuum of about 0.25 atm (200 mm Hg) is applied for a period of about 2 hours. Upon separation of the epidermis from the dermis, the epidermis layer is then pierced or removed thereby exposing the underlying dermis layer for subsequent enhanced transdermal delivery of therapeutic agents such as drugs. See for example, Svedman, U.S. Pat. No. 5,441,490.

A partial vacuum has also been used in order to determine blood gas content by applying the partial vacuum to intact skin. The partial vacuum causes "suction effusion fluid" to appear on the skin surface and vaporization of blood gases therefrom. See for example, Kaneyoshi, U.S. Pat. No. 5,417,206.

In addition to sampling blood, attempts have been made to sample interstitial fluid and to correlate the analyte content in the interstitial fluid with that in the blood. See for example, Joseph, U.S. Pat. No. 5,161,532; Erickson et al., U.S. Pat. No. 5,582,184; Brinda, U.S. Pat. No. 5,682,233; Erickson et al., U.S. Pat. No. 5,746,217 and Erickson et al., U.S. Pat. No. 5,820,570. One of the advantages of sampling interstitial fluid is that the wound created in the skin is not as deep as the wound needed for a blood sampling. Thus, interstitial fluid sampling is generally considered less invasive than blood sampling.

There have been attempts to enhance transdermal flux by mechanically puncturing the skin prior to transdermal drug delivery. See for example U.S. Pat. No. 5,279,544 issued to Gross et al., U.S. Pat. No. 5,250,023 issued to Lee et al., and U.S. Pat. No. 3,964,482 issued to Gerstel et al. These devices utilize tubular or cylindrical structures generally, although Gerstel does disclose the use of other shapes, to pierce the outer layer of the skin. Each of these devices provides manufacturing challenges and/or undesirable irritation of the skin.

A number of devices have been developed for sucking snake or insect venom out of skin pierced by a snake bite or insect bite/sting. These devices consist of a suction syringe having an open end which is placed over the skin site bit by the snake or insect. Depressing a piston/plunger causes a partial vacuum to be applied to the skin which results in at least partial extraction of the injected venom. See for example Emerit U.S. Pat. No. 4,287,819 and Emerit WO 97/14452.

However, there is still a need for even less invasive sampling of interstitial fluid for the purpose of determining analyte concentrations in the blood, for example, blood glucose concentrations. Unfortunately, less invasive techniques tend to draw smaller and smaller fluid samples making accurate analyte concentration analysis problematic.

DESCRIPTION OF THE INVENTION

The present invention provides a reproducible, high volume production, low-cost device suitable for transdermally sampling interstitial fluid for measuring the content or concentration of an agent (i.e., a body analyte such as glucose) containined therein. The device comprises a piercing member having a multiplicity of stratum corneum-piercing microblades arranged on a stratum corneum-contacting portion of the device. After the stratum corneum has been pierced by the microblades, a partial vacuum in the range of about 0.1 to about 0.8 atm, and preferably about 0.3 to about 0.7 atm, is applied to the pierced stratum corneum site. The applied negative pressure causes body fluid (i.e., interstitial fluid) to be withdrawn out of the microslits created by the microblades. The microblades have a length of about 25 to 500 $\mu$m, a width of about 10 to 400 $\mu$m, and thickness of about 10 to 100 $\mu$m. Because of their very short length, the microblades pierce only the outermost layer of the skin (i.e., the stratum corneum layer) but do not pierce sufficiently to contact the blood carrying capillaries or nerve endings. Hence, the piercing of the stratum corneum with the piercing member of the present invention causes no significant sensation (i.e., no pain) or bleeding. The body fluid which is accessed through such a shallow cut in the stratum corneum is interstitial fluid. Since glucose concentration in the interstitial fluid correlates to blood glucose levels, the present invention can be used for monitoring the blood glucose level of a human patient. Thus, the invention has particular utility in the management of diabetes.

In spite of their small size, the microblades of the piercing member can be made with an extremely reproducible size and shape so that the microslits formed by the blades puncturing the skin also have a very reproducible size and depth.

In one preferred embodiment of the invention, the piercing member comprises a sheet having a multiplicity of openings therethrough, a multiplicity of microblades integral therewith and extending downward therefrom. The microblades are pressed against the skin, causing the microblades to cut tiny shallow slits through at least the outer stratum corneum layer. Because of their small length (about 0.025 to 0.5 mm), the microblades penetrate only the outermost layer(s) of the skin to access interstitital fluid, but do not penetrate to the depth of the blood carrying capillary beds. The piercing member has a multiplicity of fluid flow pathways therethrough. A suction device connected to the skin distal side of the piercing member applies a partial vacuum in the range of about 0.1 to about 0.8 atm, and preferably about 0.3 to about 0.7 atm, through the openings in the piercing member, to the pierced stratum corneum. The partial vacuum is applied for a period of about 2 to about 30 seconds, and preferably about 5 to about 15 seconds. The partial vacuum is optionally applied through the fluid flow pathways of the piercing member in cases where the piercing member remains in situ on the skin following skin piercing. The applied suction extracts interstitial fluid out of the microslits. Optionally, the interstitial fluid can be drawn through the openings in the sheet for collection and sampling of an analyte or other substance contained therein.

MODES FOR CARRYING OUT THE INVENTION

Figure 13:
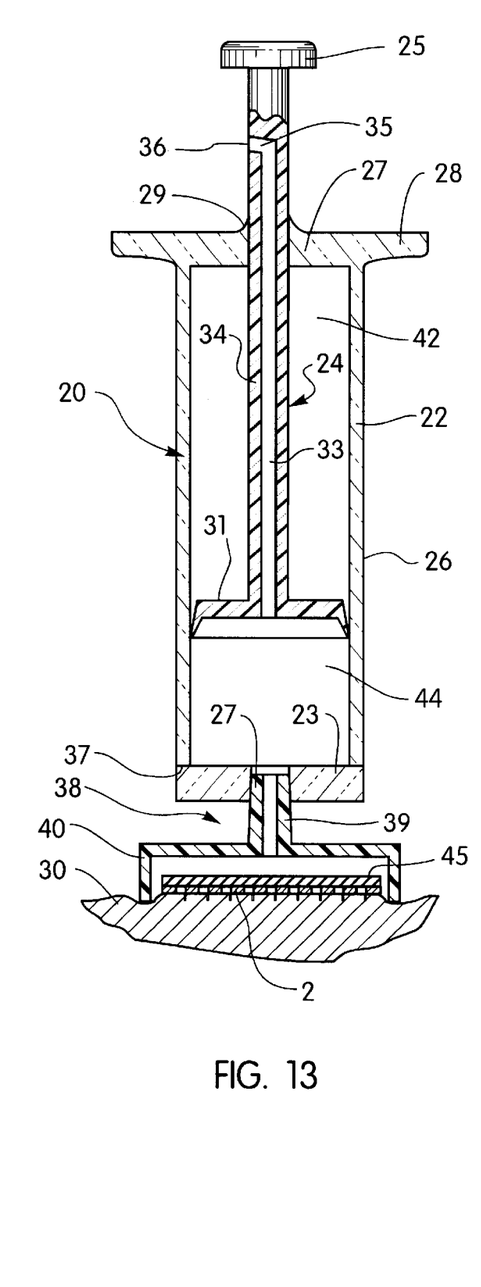
FIG. 13 is a partial sectional view of a snake venom extractor which can be used for sampling a body analyte in accordance with the present invention.
Figure 14:
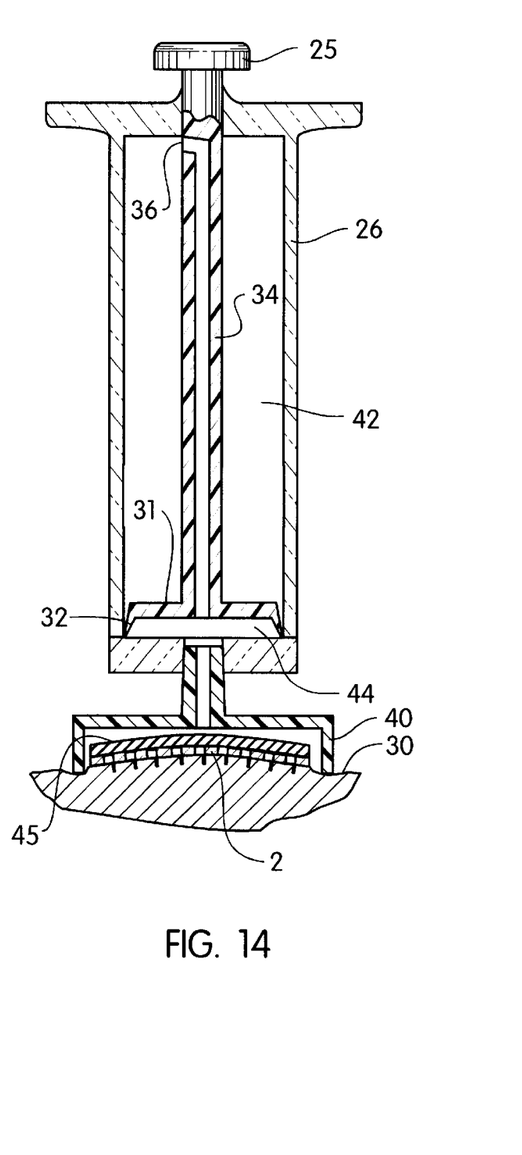
FIG. 14 is a partial sectional view of the device shown in FIG. 13 after vent 36 has passed below end portion 27 and a negative pressure is being applied to skin 30.

The present invention concerns a device and method for forming microslits through at least the outermost layer of skin and then applying a partial vacuum in the range of about 0.1 to about 0.8 atm, and preferably about 0.3 to about 0.7 atm, to the microslit skin in order to extract interstitial fluid therefrom. The interstitial fluid is extracted for purposes of sampling a body analyte (e.g., glucose) contained therein. The devices described herein are of two general types; the first type being ones in which the apparatus for forming microslits and for applying a partial vacuum are separate and distinct; and a second type in which the apparatus for forming microslits and for applying a partial vacuum are integrated into a single device. Integral skin slitting and partial vacuum applying devices are shown in FIGS. 6–12. Skin slitting devices are shown in FIGS. 1–5. Separate partial vacuum applying devices are shown in FIGS. 13 and 14.

Figure 5:
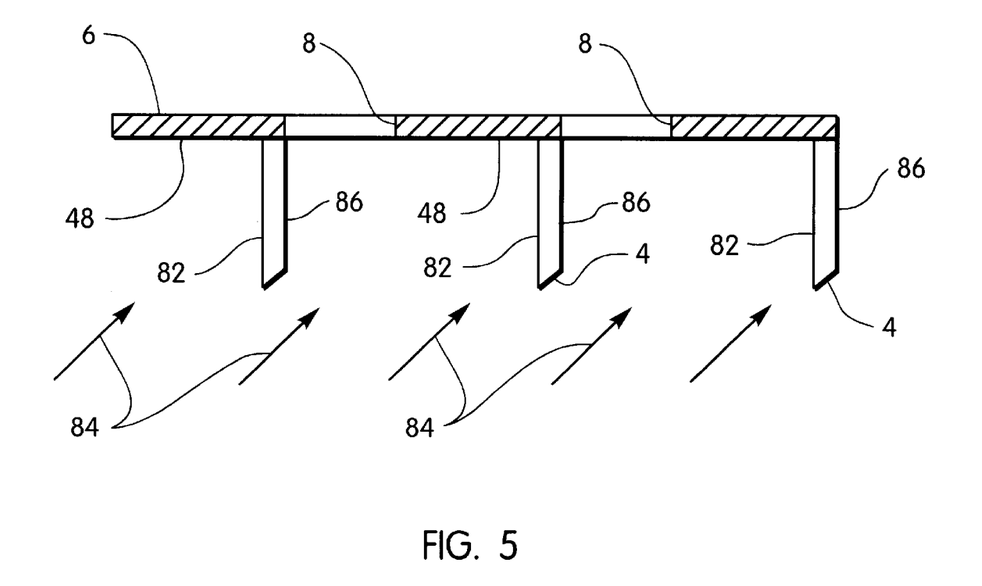
FIG. 5 is a diagrammatic cross-sectional view of another embodiment of the stratum corneum piercing member useful in the present invention.
Figure 6:
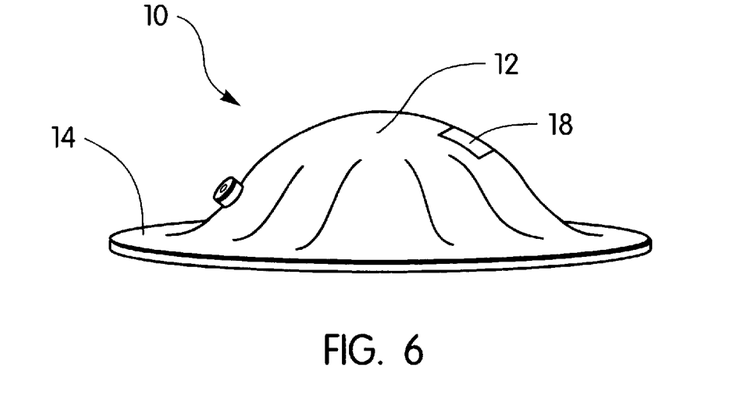
FIG. 6 is a perspective view of an integral stratum corneum-piercing and negative pressure applying device in accordance with the present invention.
Figure 7:
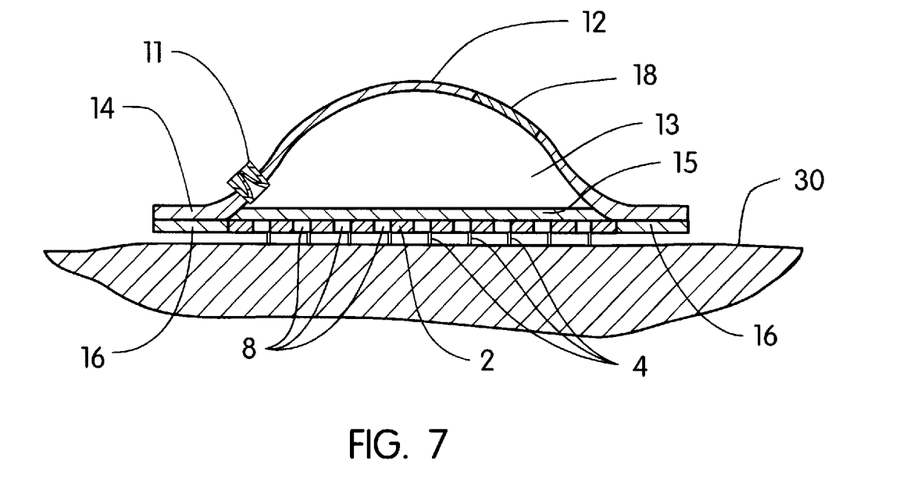
FIG. 7 is a sectional view of the device shown in FIG. 6.
Figure 8:
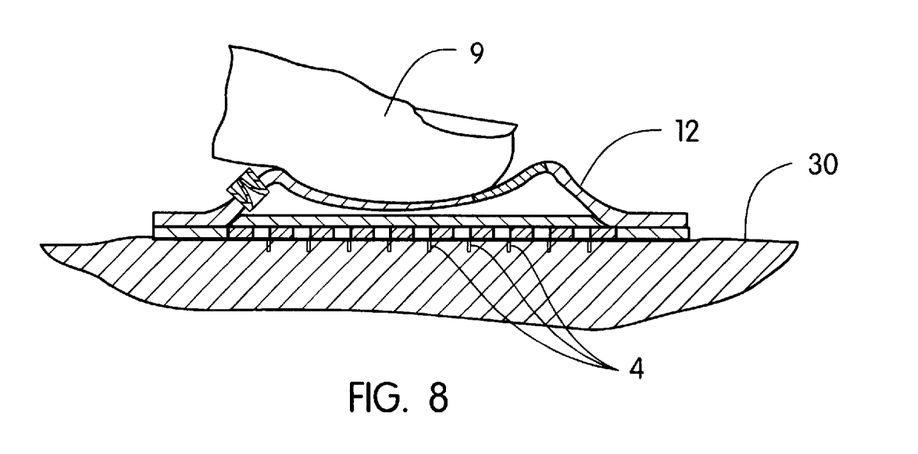
FIG. 8 is a subsequent view of the device shown in FIG. 7 as the device is being applied on the skin by finger pressure.

An integral skin slitting and partial vacuum applying device 10 is shown in FIGS. 6–8. Device 10 is comprised of a dome shaped body 12 formed of a deformable material such as a rubber or plastic. Body 12 has a flange 14 which preferably is coated on the underside with an adhesive 16 as shown in FIG. 5. Adhesive 16 is preferably a contact adhesive of the type used in adhesive bandages. Body 12 also has a one-way air valve 11 which allows air within chamber 13 to escape through valve 11 when the dome-shaped member 12 is collapsed as shown in FIG. 8. A stratum corneum piercing member 2 is attached (e.g., by gluing) to the bottom side of body 12. Member 2 is a thin metal sheet having a plurality of skin piercing microblades 4 and a plurality of openings 8 therein. Member 2 is explained in more detail in connection with FIGS. 1–5. Placed along the body distal surface of member 2 is an absorbent material 15 which acts to absorb interstitial fluid from the slit skin 30 through openings 8 in member 2. In operation, the device 10 is placed on the surface of skin 30 as shown in FIG. 7. Pressure is then applied to the top of body 12, for example by applying finger pressure by finger 9 as shown in FIG. 8. The applied downward pressure causes the microblades 4 to penetrate the outermost layer (i.e., the stratum corneum layer) of skin 30 and further causes adhesive layer 16 to contact and adhere to skin 30. The downward pressure applied by finger 9 causes the volume of chamber 13 to decrease. The air in chamber 13 is forced out of the one-way valve 11 by the applied finger pressure. Next, the finger pressure is removed and the dome-shaped member 12, due to its elastic property, springs back to its original shape (i.e., to the shape shown in FIG. 7). Alternatively, small springs (not shown in FIGS. 7 and 8) can be positioned within chamber 13 between the upper inner surface of dome 12 and piercing member 2 to assist member 12 in springing back to its original dome shape. The springing back of member 12 to its original dome shape creates a partial vacuum in the range of about 0.1 to about 0.8 atm, and preferably about 0.3 to about 0.7 atm, over that portion of the skin surface surrounded by the peripheral adhesive layer 16. This partial vacuum causes interstitial fluid to be drawn from the microslits formed by the microblades 4 through the openings 8 into the absorbent material 15.

Optionally, the device 10 includes a transparent window 18 (e.g., made from a transparent plastic material) and the material 15 includes a chemical reagent which undergoes a visual change (e.g., a color change) based upon the concentration or amount of an analyte contained in the extracted interstitial fluid. The window 18 then allows the user to see any color change occurring in absorbent material 15 without taking the device 10 apart and removing layer 15 for purposes of analyzing the concentration of the analyte absorbed.

Absorbent material 15 should be sufficiently porous to allow the negative pressure generated by release of finger pressure on body 12 to be applied through material 15 to the skin surface. For example, material 15 can be a woven or nonwoven fabric, filter paper, and similar porous absorbent materials.

Another embodiment of an integral stratum corneum piercing and partial vacuum applying device is shown in FIGS. 9–12. Device 120 is comprised of a body 122, a spring-loaded plunger unit 123 and a piston-rod unit 124 provided with an actuating knob 125. Each of these members can be made from metal or molded plastic materials.

The body 122 has a generally cylindrical shape and comprises a tube 126 having a flat end portion 127 and outer radial ears 128. The end portion 127 is provided with a central orifice 129 whose upper part is constricted by a relatively flexible thin flange. The piston 131 has on its periphery a divergent angular lip portion 132 of short axial extent and extending downwardly. An axial passageway 133 extends from the lower face of piston 131 through the major part of the length of rod 134 and is open to the exterior atmosphere by way of a vent 136. The diameter of the rod 134 is roughly equal to that of the lower part of the orifice 129 in end portion 127 such that a substantially air tight seal is formed between rod 134 and end portion 127.

The spring-loaded plunger unit 123 is comprised of (i) a spring 135 (the spring 135 is shown in compression in FIGS. 9 and 10), (ii) a plunger 137 having a flanged head 139, a sprung latch 140, and (iii) a flanged sleeve 141 having a flange 142 and a slot 145. Sleeve 141 is fixedly attached to the interior of tube 126 by welding and/or gluing the circumference of flange 142 to the inside surface of tube 126. The plunger 137 moves within sleeve 141. The plunger 137 has a central passageway 138. The passageway 138 and the slot 145 provide an airway connection between the lower chamber 144 with the skin 30. Flanged head 139 is preferably porous or has air pathways therethrough to provide an even better airway connection between the lower chamber 144 and the skin 30. Mounted on the skin-contacting face of head 139 is a piercing member 2 as described in detail and shown in FIGS. 1–5 herein.

Figure 9:
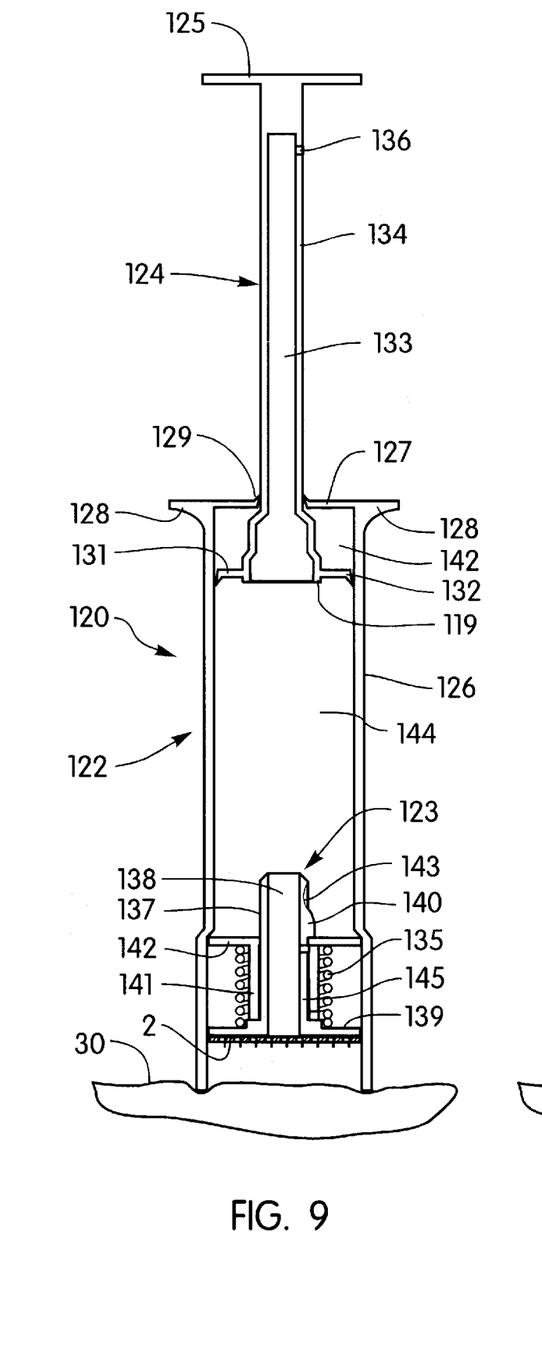
FIG. 9 is a sectional view of another embodiment of an integral stratum corneum-piercing and negative pressure applying device of the present invention.

The device 120 operates in the following manner. With the piston 131 in the upper position as shown in FIG. 9, the device 120 is held in one hand in a conventional manner with two fingers under the ears 128 and the thumb on the knob 125. The knob 125 is depressed causing the piston 131 to descend. The air within chamber 144 escapes to the exterior of device 120 by way of the passageway 133 and the vent 136.

Figure 10:
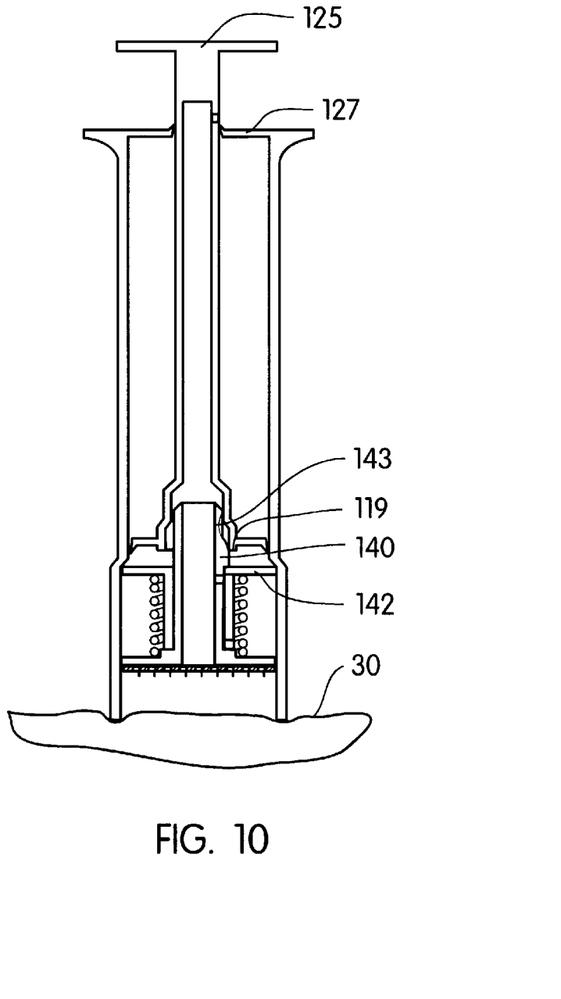
FIG. 10 is a subsequent view of the device shown in FIG. 9 with the knob 125 partially depressed.

As the piston 131 approaches the position shown in FIG. 10, the end 119 of rod 134 engages the sprung latch 140. As the knob 125 is further depressed from the position shown in FIG. 10 to the position shown in FIG. 11, the latch 140 is caused to flex at flex point 143 by the downward pressure exerted from end 119. The moving/flexing of latch 140 causes the latch 140 to clear flange 142. At that point (as shown in FIG. 11), the spring 135 is released from compression driving the head 139 and the piercing member 2 mounted thereon into the skin 30, thereby causing the microblades 4 (FIG. 1) in the piercing member 2 to pierce through the stratum corneum layer of skin 30.

Figure 11:
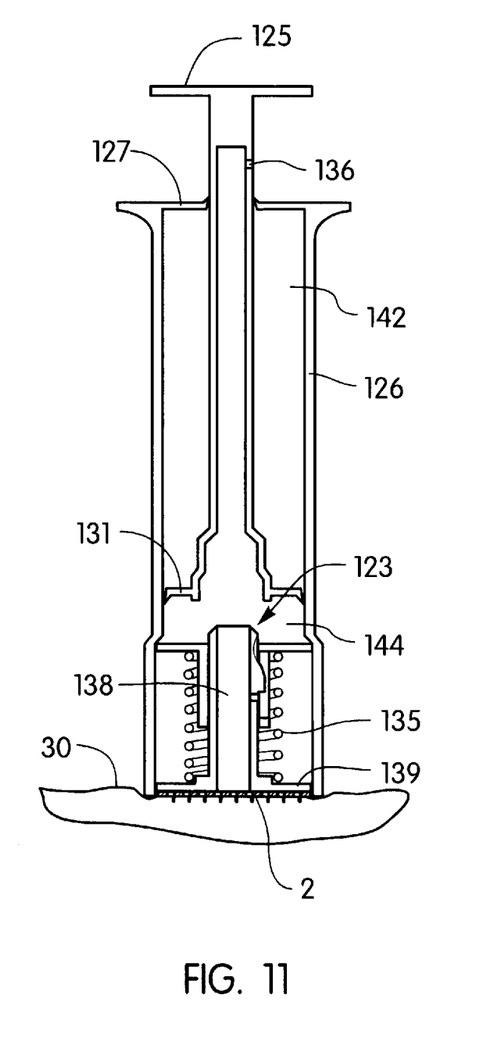
FIG. 11 is a subsequent view of the device shown in FIGS. 9–10 with the spring-loaded plunger unit 123 sprung into contact with the skin 30.
Figure 12:
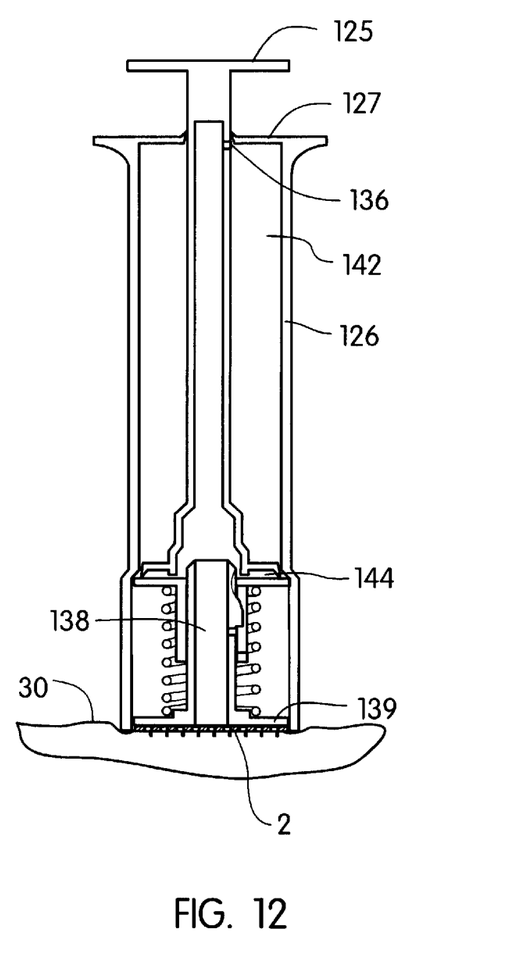
FIG. 12 is a subsequent view of the device shown in FIGS. 9–11 with the knob 125 further depressed and the vent 136 positioned below end portion 127 and a negative pressure is applied to the skin 30.

In the positions shown in FIGS. 10 and 11, the vent 136 is still positioned above the end portion 127. However, further depression of knob 125 causes the vent 136 to pass just below the end portion 127 (see FIG. 12). The chamber 142 (which is now under a partial vacuum due to the downward movement of piston 131) is connected to the lower chamber 144 and to the skin surface 30 through the central passageway 138, the slot 145 and optionally through the pores/air pathways through head 139. This causes a partial vacuum in the range of about 0.1 to about 0.8 atm, and preferably about 0.3 to about 0.7 atm, to be applied to that portion of the skin surface 30 located within the confines of the skin proximal end of tube 126. Because the piercing member 2 has a plurality of openings 8 therethrough (see FIG. 1), the partial vacuum existing within the central passageway 138 is applied to the skin surface through the openings in the piercing member 2. Head 139 is preferably porous, or alternatively provided with a plurality of air passageways therethrough, so that the negative pressure is preferably applied across the entire surface area of piercing member 2.

As an alternative to the integral stratum corneum-piercing and partial vacuum applying devices 10 and 120 shown in FIGS. 6–12, the piercing member 2 can be separately applied to the skin 30 to form microslits therein and then removed following microslit formation. Following removal of the member 2, a separate partial vacuum applying device such as that illustrated in FIGS. 13 and 14 can be applied on the microslit skin 30 in order to extract interstitial fluid. Following extraction, the interstitial fluid can be collected (e.g., by placing an absorbent material over the microslit skin) upon removal of the negative pressure device and then analyzed for analyte content. One device which can be used to apply a partial vacuum to the surface of the skin in accordance with the present invention is disclosed in Emerit U.S. Pat. No. 4,287,819 and sold commercially by Sawyer Products of Safety Harbor, Fla. under the tradename Extractor® for use in extracting snake or insect venom. The Extractor® device is shown in FIGS. 13 and 14 and comprises a syringe 20 with four members: a body 22, a cap 23 and piston-rod unit 24 provided with an actuating knob 25. Each of these members can be made from metal or molded plastic materials.

The body 22 has a generally cylindrical shape and comprises a tube 26 having a flat end portion 27 and outer radial ears 28. For convenience of description, it will be assumed that the axis is vertical and that the end portion 27 and the ears 28 are at the upper end of the tube 26. The other end of the latter is open. The end portion 27 is provided with a central orifice 29 whose upper part is constricted by a relatively flexible thin flange. The cap 23 is a disk whose outside diameter is equal to that of the tube 26 and comprises at its center an upwardly convergent orifice 21. The piston 31 has on its periphery a divergent annular lip portion 32 of short axial extent and extending downwardly. An axial passageway 33 extends from the lower face of piston 31 through the major part of the length of the rod 34 and terminates in an elbow 35 and radially opens out by way of a vent 36. The diameter of the rod 34 is roughly equal to that of the lower part of the orifice 29 of the end portion 27.

The syringe 20 is assembled in the following manner:

The rod 34 is inserted in the tube 26 through the bottom of the latter and made to pass through the orifice 29. The flange of the latter is then deformed upwardly and forms an annular lip portion 32 which hermetically bears against the rod 34 while it allows the sliding of the latter, with the lip portion 32 of the piston 31 sliding hermetically against the inner wall of the tube 26. The knob 25 is then secured, for example by adhesion, to the upper end of the rod 34 and the cap 23 is likewise secured to the lower planar end face 37 of the tube 26.

This syringe 20 operates in the following manner:

With the piston 31 in the upper position, the syringe 20 is held in one hand in the conventional manner with two fingers under the ears 28 and the thumb on the knob 25. The skirt portion 40 of syringe 20 is placed over the microslit skin site. When using the syringe 20, it is possible to leave the piercing member 2 in place as shown in FIGS. 13 and 14. Preferably, the piercing member 2 carries an absorbent material with an analyte reagent on the skin distal surface thereof. For example, material 45 may be composed of a similar material as material 15 described in connection with device 10 and contains a glucose reagent which changes color upon reaction with the glucose contained in the extracted interstitial fluid. Alternatively, the skirt portion 40 of syringe 20 can be placed on the microslit skin site after application and removal of the skin piercing member 2. In such a use, the partial vacuum applied by syringe 20 causes the interstitial fluid to be drawn out of the microslits in the stratum corneum and must subsequently be collected or otherwise placed on a reagent test strip for analysis of the body analyte contained therein.

The knob 125 is depressed causing the piston 31 to descend. The air within chamber 44 escapes to the atmosphere by way of the passageway 33 and the vent 36. Possibly, it may also escape by way of the orifice 21 if the latter is opened to the atmosphere.

At the end of the travel of the piston 31, when it abuts against the cap 23, the vent 36 passes just below the end portion 27 (FIG. 14). The chambers 42 and 43 of the body are then put into communication with each other by way of the passageway 33 so that the vacuum created in the upper chamber 42 by the descent of the piston 31 produces a sudden partial vacuum in the lower chamber 43 the volume of which is at this moment very small.

An end member 38 may be fitted in the orifice 21, this member 38 comprising a frustoconical upper connector 39 provided axially with a cylindrical lower skirt portion 40 which is open on the underside and connected to the connector 39 by a flange. If this skirt portion 40 is applied on the skin surface before the piston has been shifted downwardly, or at least before the piston reaches the cap 3, the end of the descent of the piston results in a sudden partial vacuum in the range of about 0.1 to about 0.8 atm, and preferably about 0.3 to about 0.7 atm, whereby it is possible to draw off the interstitial fluid from the microslit skin. The operation of the syringe may be carried out on oneself in a very convenient manner on practically any part of the body, since one hand is sufficient to create the suction.

In order to extract a sufficient quantity of interstitial fluid for purposes of glucose sampling, it has been found that a partial vacuum of about 0.1 to about 0.8 atm, preferably about 0.3 to about 0.7 atm, over periods of about 2 to about 30 seconds, preferably about 5 to about 15 seconds, are sufficient to extract microliter quantities which can be used to determine the amount or concentration of the sampled analyte. It should be noted that applying a partial vacuum in the range of about 0.1 to 0.8 atm for periods of less than one minute does not result in the formation of a suction blister, which typically requires application of 0.25 atm over at least about 2 hours.

Figure 1:
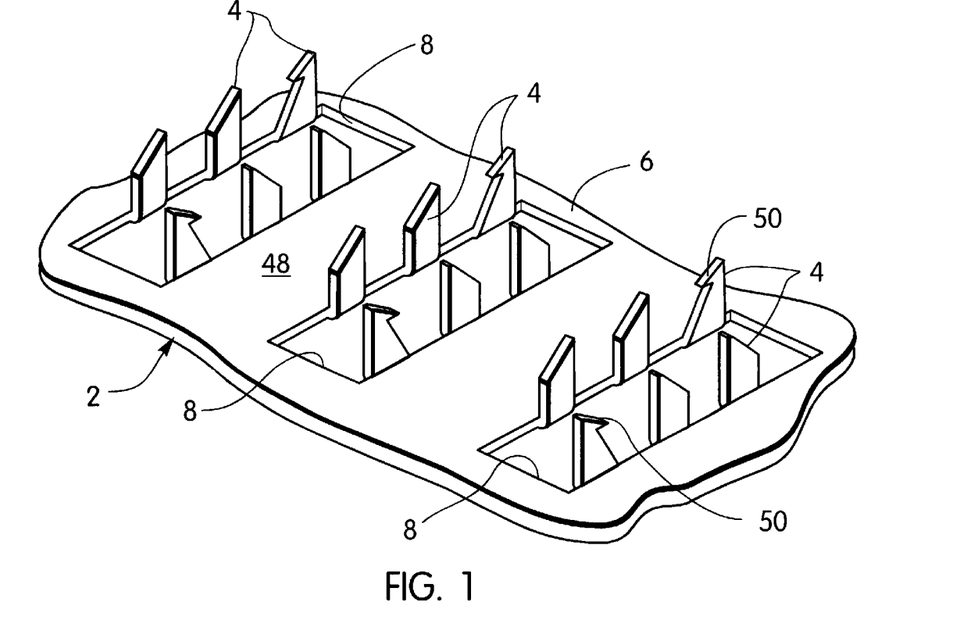
FIG. 1 is an enlarged perspective view of the skin proximal side of a stratum corneum piercing member useful in the present invention.

The stratum corneum piercing member 2 is shown, in greatly enlarged scale, in FIGS. 1–5. Referring specifically to FIG. 1, member 2 comprises a plurality of microblades 4 (i.e., a microblade array) extending downward from one surface of a sheet or plate 6 (see FIG. 1 in which member 2 is in an inverted position to show the microblades). The microblades 4 penetrate the stratum corneum of the epidermis when pressure is applied to the device to increase the sampling of a substance through a body surface (i.e., the skin of an animal and particularly a human).

The microblades 4 are generally formed from a single piece of material and are sufficiently sharp and long for puncturing the stratum corneum of the skin. In one embodiment, the microblades 4 and the sheet 6 are essentially impermeable or are impermeable to the passage of an agent. The sheet 6 is formed with a multiplicity of openings 8 between the microblades 4 for enhancing the movement of an agent therethrough. During agent (e.g., body analyte) sampling, the analyte (or interstitial fluid containing the analyte) migrates from the body through the microslits in the stratum corneum which are cut by the microblades 4. In one embodiment, the opening 8 corresponds to the portion of the sheet 6 occupied by each of the microblades 4 prior to the microblades 4 being transpositioned into the downward depending position. The number of microblades 4 per opening 8 can be any number, preferably however from 1 to about 30 blades per opening and more preferable from 1 to 3 microblades per opening. Furthermore, the number of openings 8 per piercing member 2 and the number of blades per piercing member 2 are independent.

As is best shown in FIG. 1, the microblades 4 have a thickness which is much smaller than the width of the microblades near their base, i.e., near the point where the microblades 4 are attached to the plate 6. This microblade geometry provides maximum agent percolation area with a minimum blade penetration area, and hence less tissue damage. The agent percolation area is the skin area in contact with the blades which provides for interstitial fluid flow and agent flux through the skin. The microblades are preferably shaped with the largest possible surface area with a minimal cross-sectional area so as to give the largest possible percolation area. Thin microblades are better than round protrusions for this purpose because for the same cross-section, a thin microblade produces more percolation area and less tissue damage than a round protrusion. This is an advantage over round (cross section) sin piercing elements such as needles and tubes. Thin microblades also require less insertion force than round protrusions. The width of each microblade can be any of a range of widths. The widths can be different from microblade to microblade in the array pattern. Likewise, the width can be variable along the length of the microblade. The width of the microblade at the intersection of the microblade and the body surface after the microblade array has been inserted is preferably in the range of about 25 $\mu$m to about 500 $\mu$m, more preferably about 50 $\mu$m to about 400 $\mu$m, more preferably 100 $\mu$m to about 300 $\mu$m.

Figure 4:
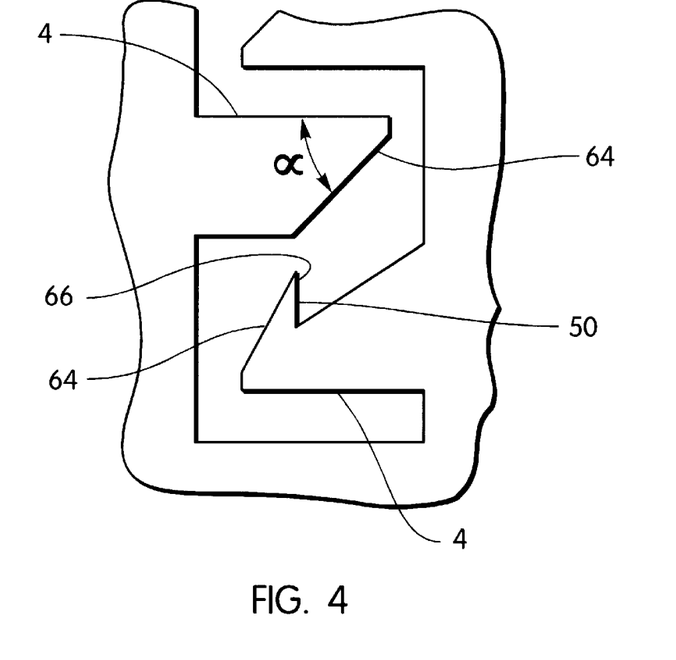
FIG. 4 is an enlarged view of a portion of the blades of the blade array pattern of FIG. 3.

Preferably, as best shown in FIG. 4, the microblades 4 are also provided with slanted (i.e., angled) leading edges 64 to further reduce the insertion force required to press the microblades into the skin tissue. The angle of the leading edge is designated as $\alpha$. The slanted leading edges produce a cut through the skin tissue that is equal to the full width of the microblade 4 while reducing the amount of metal that is in the skin tissue. In other words, a flat leading edge (i.e., $\alpha$ is 90°) produces a microblade with a larger amount of blade material in the skin tissue than is produced by a microblade having a slanted leading edge. The leading edges of each microblade can all be the same angle or can be at different angles as shown in FIG. 4. The angle $\alpha$ of each leading edge can be any angle between about 10° to 90°, preferably between about 10° to 60°, more preferably about 10° to 40°. The leading edge can also be segmented into two sections at different angles. For example, the first segment can have an angle $\alpha$ between about 10° to 40° and then transition to a second segment having an angle between 20° to 60°. Alternatively, the leading edge of each microblade can be arcuate (i.e., curved) in shape, having, for example, a convex or concave shape. In one embodiment, the leading edge is a curved tip across the entire width of the microblade.

Optionally, the piercing member 2 improves the attachment of the device to the skin so that the percolation areas and a continuous pathway are preserved during movement of the body surface. In the embodiment shown in FIG. 2, projections in the form of barbs 50 on at least one of the microblades 4 assist in anchoring the piercing member 2 and any corresponding device or structure used in combination therewith to the skin. Barbs 50 can be on any number of the microblades from one microblade to all microblades.

The microblades 4 can be formed using a photo-etching process, which is described in detail in Cormier et al., WO 97/48,440, the disclosures of which are incorporated herein by reference. This process allows the microblades 4 to be reproducibly formed on a very small (i.e., tens of microns) scale.

Figure 3:
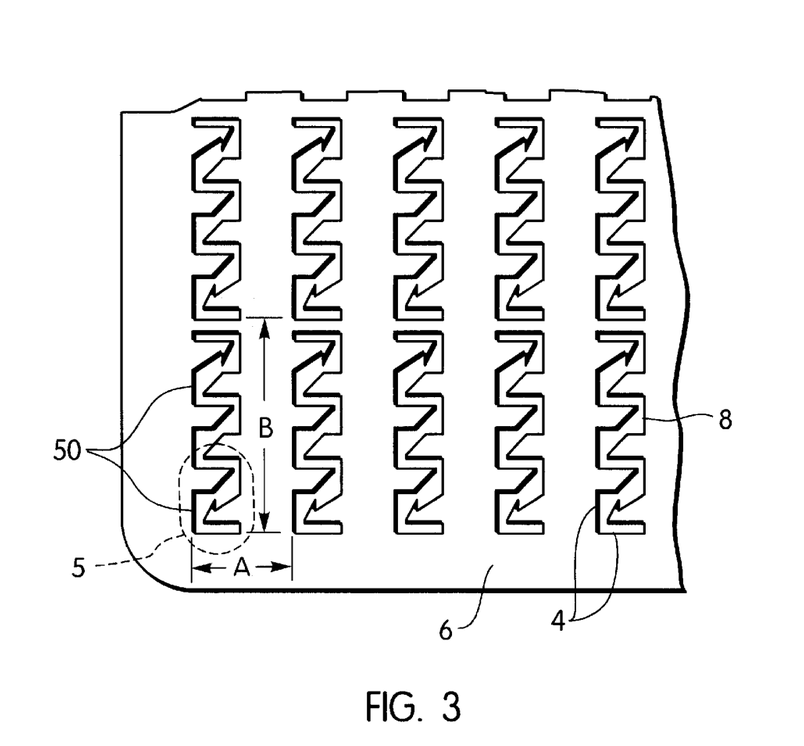
FIG. 3 is a partial top plan view of the stratum corneum piercing member of FIG. 1, before bending/punching the microblades out of the plane of the sheet.

The plurality of microblades 4 for puncturing the stratum corneum are present on one surface 48 of the piercing member 2 in any predetermined arrangement, for example, as a cluster of microblades spaced in rows having any desired number, or in any spaced apart relation of one microblade to each other. The piercing member 2 shown in FIG. 1 is produced by the pattern shown in FIG. 3. In the embodiment of FIG. 3, there are six microblades 4 in each opening 8 in sheet 6. Each opening 8 in this embodiment is 1 mm long and 300 µm wide. Correspondingly, the width of each microblade is between about 137.5 µm to about 175 µm and the length is about 250 µm. The required length of the microblades is subject to variation of the body surface being penetrated and corresponds to the natural thickness of the stratum corneum, for one of the principle features of the invention is that the microblades are to penetrate the stratum corneum into the epidermis. Usually, the microblades will be about 25 µm to about 500 µm in length, with the length for most applications being between about 50 µm to about 400 µm.

Generally, the microblades 4 are at an angle of about 90° to the surface 48 of the sheet 6 after being punched, but they can be disposed at any angle forward or backward from the perpendicular position that will facilitate penetration of the stratum corneum.

In one embodiment (FIG. 5), anchoring of the device is achieved by coating the surface 48 of sheet 6, and optionally also the surface 82 of each microblade 4, with an adhesive. One method of producing this embodiment comprises spraying the adhesive on the piercing member 2 along the direction indicated by arrows 84. In this embodiment, the agent is free to pass through the openings 8 and along surface 86 of each microblade unencumbered by the adhesive. It is also possible to apply the adhesive on only surface 48 and not on the microblade surfaces 82. This can be accomplished, for example, by applying the adhesive onto surface 48 after the microblades 82 have been punched by spraying the adhesive in a direction which is parallel to the axis of the blades 82. It is further possible to apply the adhesive only on the microblade surfaces 82 and not on the surface 48 of sheet 6 in order to anchor the device, although this last design is the least preferred adhesive anchoring means.

Figure 2:
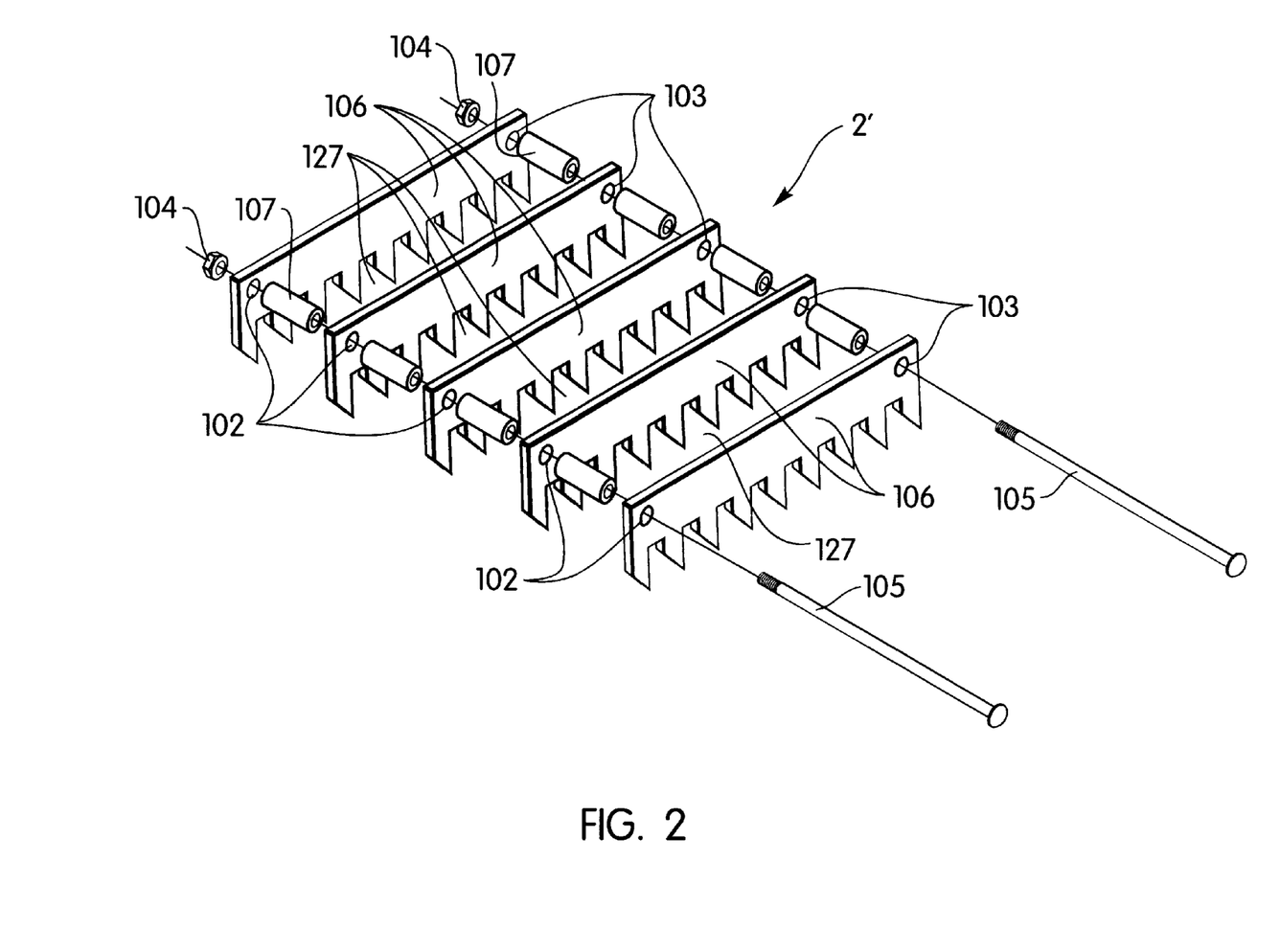
FIG. 2 is a perspective exploded view of another embodiment of a stratum corneum piercing member useful in the present invention.

All of the piercing members 2 illustrated in FIGS. 1 and 3–5 have the microblades 4 oriented at an angle relative to the plane of sheet 6 and the sheet 6 oriented approximately parallel to the skin surface. Another embodiment of a piercing member 2' is shown in FIG. 2 and has the microblades in the same plane of the sheet, with the plane of the sheet oriented at an angle (e.g., perpendicular) to the skin surface. The sheet 106 has a plurality of microblades in the same plane as the sheet and extending outward from a body proximal edge of the sheet for piercing the body surface. Piercing member 2' comprises a plurality of individual sheets 106 stacked and fastened together. Each of the sheets 106 has a pair of holes 102, 103, through which bolts 105 are inserted. Spacers (e.g., tubes) 107 are positioned between each adjacent part of sheets 106 to form voids 108 therebetween. The spaced sheets 106 are held together as a unit by securing nuts 104 on the ends of bolts 105, or using other known fasteners. The voids 108 can be filled with a reservoir matrix material (e.g., a gel or an absorbent material of the type used for material 15 in FIG. 7) adapted to receive the body analyte to be sampled. Those skilled in the art will appreciate that spacers having other than tube-like configurations (e.g., square or rectangular blocks) can also be used to provide voids 108 between adjacent sheets 106. Furthermore, more than two sets of bolts 105, or other fastening pins, may be used to secure the sheets 106 and spacers 105 together. The thin sheet 106 transmits force applied to a body distal edge of the sheet 106 to the microblades with substantially less dissipation of the application force in the thin sheet than the piercing member 2 shown in FIG. 1. The rigid structure formed by the assembled and fastened thin sheets 106 provides assured transmittance of an externally applied load to the microblades without wasting energy in deflection of any portion of the device for easier, complete and reproducible skin penetration. The improved penetration of the skin by the microblades because of the rigid structure formed by the thin sheet 106 is particularly beneficial in producing increased agent flux. The transmitted load provides nearly complete penetration by all of the microblades so as to produce a substantial number of microslits in the stratum corneum for continued and reproducible transdermal agent flux.

The sheet 106 with the plurality of microblades can be manufactured more easily and less expensively than the designs comprised of a thin sheet 6 (FIG. 1) having microblades 4 punched perpendicularly therefrom since there is no need for a separate punching operation.

The sheet and blades for the microblade device 2 can be made from materials that have sufficient strength and manufacturability to produce blades, such as, glasses, silicon, ceramics, rigid polymers, metals and metal alloys. Examples of metals and metal alloys include but are not limited to stainless steel, iron, steel, tin, zinc, copper, platinum, aluminum, germanium, nickel, zirconium, titanium and titanium alloys consisting of nickel, molybdenum and chromium, metals plated with nickel, gold, rhodium, iridium, titanium, platinum, and the like. An example of glasses includes a devitrified glass such as "Photoceram" available from Corning in Corning, N.Y. Examples of rigid polymers include but are not limited to polystyrene, polymethylmethacrylate, polypropylene, polyethylene, "Bakelite", cellulose acetate, ethylcellulose, styrene/acrylonitrile copolymers, stryrenetbutadiene copolymers, acrylonitrile/butadiene/styrene (ABS) copolymers, polyvinyl chloride and acrylic acid polymers including polyacrylates and polymethacrylates.

Very dense patterns can be created with unit cells wherein a unit cell has a width A and a length B as illustrated in FIG. 3. In one embodiment (not shown), the pattern has the following characteristics: a unit cell area of 0.63 mm by 3.8 mm; the lineal length of a cut in a unit cell is approximately equal to 15 mm; and the open skin length per square centimeter is 625 mm.

The microblades of the present invention make an elongated, thin microcut (i.e., a slit) in the skin surface because the blades have a small thickness (relative to their width and length) resulting in a minimal blade cross-sectional area for the portions of the blade in the skin. The geometry of the microblades 4 results in minimal blade volume in the skin with maximal blade surface area in the skin. The advantages of the present invention include, but are not limited to: (1) the thin blade geometry produces the maximum agent percolation area for a given cross-section of the blade; (2) minimal tissue damage occurs because the amount of blade material in the skin and hence the volume loading is minimized; (3) slanted leading edges (or equivalent pointed shapes) further minimize the amount of volume loading or tissue damage while preserving a large percolation area; (4) for a given volume loading, the larger the surface area, the larger the frictional retaining force in the skin; and (5) for a given desired percolation area, there are fewer blades necessary and therefore the force on each tip is higher making skin penetration easier.

The number of microblades and openings of any of the embodiments of the device 2 is variable with respect to the desired flux rate, agent being sampled, the sampling device used, and other factors as will be evident to one of ordinary skill in the art. In general, the larger the number of blades per unit area (i.e., the blade density), the more distributed is the flux of the agent through the skin because there are a greater number of agent-conveying pathways through the skin. Consequently, the smaller the number of blades per unit area, the more concentrated is the flux of the agent through the skin because there are fewer pathways. Preferably, the blade density is at least about 20 blades/cm$^2$ and less than about 1000 blades/cm$^2$, more preferably at least about 100 blades/cm$^2$, still more preferably at least about 200 blades/cm$^2$. In those embodiments comprised of a sheet 6 with openings 8 therein, the number of openings per unit area through which the agent passes is at least about 10 openings/cm$^2$ and less than about 1000 openings/cm$^2$. In one embodiment, the present invention produces a percolation area of about 0.005 to 0.05 cm$^2$/cm$^2$ of body surface, preferably about 0.01 cm$^2$/cm$^2$ of body surface.

The sampled analyte is generally collected in a reservoir matrix for (e.g., subsequent) analysis. The reservoir matrix should be compatible with the sampled agent and any materials (e.g., analyte reagents) contained therein. When sampling an analyte contained in interstitial fluid, any conventional water absorbing material (e.g., paper or absorbent hydrophilic polymers) can be used as the sampling reservoir matrix.

The devices of the present invention can be used to sample any of a variety of agents through a body surface including, but not limited to glucose, body electrolytes, alcohol, blood gases, and illicit substances such as drugs of abuse. The terms "substance", "agent" and "analyte" are used interchangeably herein and broadly in mammals include substances such as glucose, electrolyte, alcohol, illicit drugs, etc. that can be sampled through the skin of animals including humans and primates, avians, valuable domestic household, sport or farm animals, or for sampling from laboratory animals such as mice, rats, guinea pigs, and the like.

The following example is merely illustrative of the present invention and should not be considered as limiting the scope of the invention in any way, as this example and other equivalents thereof will become apparent to those versed in the art and in light of the present disclosure, drawings, and the accompanying claims.

EXAMPLE

Stratum corneum piercing and interstitial fluid extraction by means of applied negative pressure was performed on the ventral forearm of a normal male volunteer. The stratum corneum piercing was achieved using a spring-loaded applicator head having a stratum corneum-piercing member of the general configuration shown in FIG. 1 mounted thereon. The piercing member was comprised of a stainless steel sheet having a thickness of 0.025 mm (1 mil). The sheet had an area of 1 cm$^2$ and a microblade density of 190 microblades/cm$^2$. The plate had 190 openings/cm$^2$ and 1 microblade per opening in the sheet and each microblade had a length of 0.4 mm. Immediately after application of the piercing member, the applicator and piercing member were removed from the skin site and an Extractor® (sold by Sawyer Products of Safety Harbor, Fla.) was used to apply negative pressure to the pierced skin site. The Extractor® was fitted with a cup having a size of 2 cm$^2$. A negative pressure of about 0.2 atm was applied for about 5 seconds. Visual observation indicated that interstitial fluid, mixed with some blood, oozed at the surface of the skin immediately after application of the negative pressure. After removal of the Extractor® from the skin site, a First Choice™ reagent strip for blood glucose testing (sold by Polymer Technology International of Issaquah, Wash.) was applied on the skin site for a few seconds. Color change of the testing strip was observed immediately and revealed normal blood glucose levels.

Identical results were produced using a negative pressure of about 0.5 atm, which is more acceptable from a sensation standpoint. Identical results were also obtained at 0.5 atm using similar microblade arrays having microblade lengths of 400 $\mu$m, 300 $\mu$m and 230 $\mu$m. All applications were rated painless and acceptable by the subject.

As a comparison, the First Choice™ reagent test strip was applied to skin sites that were treated to either microblade array piercing or negative pressure, but not both. In all of these comparative tests no color change of the glucose test strip was observed.

While the invention has been described in conjunction with the preferred specific embodiments thereof, it is to be understood that the foregoing description as well as the example are intended to illustrate and not limit the scope of the invention. Other aspects, advantages and modifications within the scope of the invention will be apparent to those skilled in the art to which the invention pertains.

What is claimed is:

1. An apparatus for piercing the stratum corneum and withdrawing a body fluid therethrough for sampling an agent in the fluid, comprising:

a piercing member having a plurality of stratum corneum-piercing microblades, wherein the microblades having a length sufficient to pierce the stratum corneum to a depth in the range of about 25 $\mu$m to about 400 $\mu$m, the microblades being arranged on a stratum corneum-contacting portion of the apparatus, the piercing member having a plurality of fluid flow pathways therethrough, and     a partial vacuum applying device connected to the piercing member for applying a partial vacuum in a range of about 0.1 atm to about 0.8 atm over a period of about 2 seconds to about 30 seconds through the fluid flow pathways to the pierced stratum corneum for withdrawing the body fluid.

2. The apparatus of claim 1, wherein the agent is selected from the group consisting of body electrolytes, illicit drugs and glucose.

3. The apparatus of claim 1, the body fluid is interstitial fluid.

4. The apparatus of claim 3, wherein the body fluid is substantially free of blood.

5. The apparatus of claim 1, wherein the piercing member comprises a sheet having a multiplicity of openings therethrough and a multiplicity of microblades extending downward therefrom.

6. The apparatus of claim 5, wherein the microblades are located along peripheries of the openings through the sheet.

7. The apparatus of claim 1, wherein the piercing member comprises a plurality of spaced sheets, each of the sheets having a stratum corneum-contacting edge having a plurality of the microblades extending therefrom, the fluid flow pathways being voids between adjacent sheets.

8. The apparatus of claim 1, wherein the piercing member has about 20 microblades/$cm^2$ to about 1000 microblades/$cm^2$.

9. The apparatus of claim 1, wherein the partial vacuum applying device applies a partial vacuum of about 0.3 atm to about 0.7 atm.

10. The apparatus of claim 1, wherein the partial vacuum applying device applies the partial vacuum for a period of about 5 seconds to about 15 seconds.

11. The apparatus of claim 1, wherein the partial vacuum applying device comprises a suction cup sealingly mounted on the piercing member.

12. The apparatus of claim 11, wherein the suction cup is composed of a flexible material, the cup resiliently recovering its size and shape after applying a compressive force thereto.

13. The apparatus of claim 1, wherein the suction cup includes a one-way air valve.

14. The apparatus of claim 1, wherein the partial vacuum applying device comprises an animal venom extractor.

15. The apparatus of claim 14, wherein the animal venom extractor comprises a syringe body having a stratum corneum engaging skirt and a piston and plunger having an air passageway extending therethrough.

16. The apparatus of claim 1, wherein the partial vacuum applying device comprises a syringe body having an open stratum corneum-engaging end and a piston-plunger assembly having an air passageway extending therethrough, the syringe body also containing a spring-loaded plunger unit having the microblades mounted thereon.

17. A method of sampling an agent, comprising:
   a) piercing the stratum corneum with a piercing member having a plurality of microblades wherein the microblades having a length sufficient to pierce the stratum corneum to a depth in the range about 25 $\mu$m to about 400 $\mu$m;
   b) applying a partial vacuum in the range of about 0.1 atm to about 0.8 atm to the pierced stratum corneum over a period of about 2 seconds to about 30 seconds to withdraw a body fluid containing the agent; and
   c) analyzing for the agent.

18. The method of claim 17, wherein the agent is selected from the group consisting of body analytes, electrolytes, blood gases, illicit drugs, licit drugs and glucose.

19. The method of claim 17, the body fluid is interstitial fluid.

20. The method of claim 19, wherein the fluid is substantially free of blood.

21. The method of claim 17, wherein the piercing member comprises a sheet having a multiplicity of fluid flow pathways therethrough and a multiplicity of microblades extending therefrom.

22. The method of claim 21, wherein the partial vacuum is applied through the fluid flow pathways to withdraw the body fluid through the fluid flow pathways.

23. The method of claim 17, including collecting the body fluid.

24. The method of claim 17, wherein the partial vacuum is about 0.3 atm to about 0.7 atm.

25. The method of claim 17, wherein the partial vacuum is applied for a period of about 5 to about 15 seconds.

* * * * *